United States Patent
Oganesian et al.

(10) Patent No.: US 11,963,971 B2
(45) Date of Patent: *Apr. 23, 2024

(54) COMBINATION DECITABINE AND CEDAZURIDINE SOLID ORAL DOSAGE FORMS

(71) Applicant: Otsuka Pharmaceutical Co., Ltd., Tokyo (JP)

(72) Inventors: Aram Oganesian, Dublin, CA (US); Nipun Davar, Pleasanton, CA (US); Jim Hwaicher Kou, San Jose, CA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/309,440

(22) Filed: Apr. 28, 2023

(65) Prior Publication Data

US 2023/0263818 A1 Aug. 24, 2023

Related U.S. Application Data

(63) Continuation of application No. 17/904,536, filed as application No. PCT/US2021/019310 on Feb. 24, 2021.

(60) Provisional application No. 62/981,304, filed on Feb. 25, 2020.

(51) Int. Cl.
| | | |
|---|---|---|
| *A61K 31/706* | (2006.01) | |
| *A61K 9/00* | (2006.01) | |
| *A61K 9/20* | (2006.01) | |
| *A61K 9/48* | (2006.01) | |
| *A61K 31/20* | (2006.01) | |
| *A61K 31/7016* | (2006.01) | |
| *A61K 31/717* | (2006.01) | |

(52) U.S. Cl.
CPC .......... *A61K 31/706* (2013.01); *A61K 9/0056* (2013.01); *A61K 9/20* (2013.01); *A61K 9/4891* (2013.01); *A61K 31/20* (2013.01); *A61K 31/7016* (2013.01); *A61K 31/717* (2013.01)

(58) Field of Classification Search
None
See application file for complete search history.

(56) References Cited

U.S. PATENT DOCUMENTS

| | | |
|---|---|---|
| 2006/0074046 A1 | 4/2006 | Redkar et al. |
| 2018/0120304 A1 | 5/2018 | Rao et al. |
| 2020/0085848 A1 | 3/2020 | Keer et al. |

OTHER PUBLICATIONS

Garcia-Manero, Guillermo, et al. "Pharmacokinetic exposure equivalence and preliminary efficacy and safety from a randomized cross over phase 3 study (ASCERTAIN study) of an oral hypomethylating agent ASTX727 (cedazuridine/decitabine) compared to IV decitabine." Blood 134 (2019): 846.*

Debotton, Nir, and Arik Dahan. "Applications of polymers as pharmaceutical excipients in solid oral dosage forms." Medicinal research reviews 37.1 (2017): 52-97.*

Garcia-Manero, Guillermo, et al. "A phase 2 dose-confirmation study of oral ASTX727, a combination of oral decitabine with a cytidine deaminase inhibitor (CDAi) cedazuridine (E7727), in subjects with myelodysplastic syndromes (MDS)." Blood 130 (2017): 4274.*

"International Preliminary Report on Patentability corresponding to International Application No. PCT/US2021/019310 dated Sep. 9, 2022".

"International Search Report and Written Opinion corresponding to International Application No. PCT/2021/019310 dated May 10, 2021".

Garcia-Manero, Guillermo, et al., "A Phase 2 Dose-Confirmation Study of Oral ASTX727, a Combination of Oral Decitabine with a Cytidine Deaminase Inhibitor (CDAi) Cedazuridine (E7727), in Subjects with Myelodysplastic Syndromes (MDS)", Bood 130(Suppl 1):4274 (Dec. 7, 2017).

Savona, Michael R, et al., "An Oral Fixed-Dose Combination of Decitabine and Cedazuridine in Myelodysplastic 1-4 Syndromes: a Multicentre, Open-Label, Dose-Escalation, Phase I Study", Lancet Haematol. 6(4):e194-e203 (Apr. 2019).

"Extended European Search Report corresponding to European Application No. 21761883.4 dated Oct. 30, 2023".

Garcia-Manero, Guillermo, et al., "Pharmacokinetic Exposure Equivalence and Preliminary Efficacy and Safety from a Randomized Cross over Phase 3 Study (ASCERTAIN study) of an Oral Hypomethylating Agent ASTX727 (cedazuridine/decitabine) Compared to IV Decitabine", PRESENTATION, 61st ASH Annual Meeting Abstract 846 (Dec. 10, 2019) 15 pages.

* cited by examiner

*Primary Examiner* — Patrick T Lewis
(74) *Attorney, Agent, or Firm* — Myers Bigel, P.A.

(57) ABSTRACT

Embodiments of the present invention provide solid oral dosage forms that upon daily administration to a subject provide plasma levels of decitabine with a 5-day AUC for decitabine that is equivalent to the 5-day AUC for a daily IV dose of decitabine of 20 mg/m² administered as a one hour (1 h) infusion. Also provided according to embodiments of the present invention are solid oral dosage forms wherein upon daily administration to a subject provides a pharmacodynamic effect that is equivalent to the pharmacodynamic effect for a daily intravenous dose of decitabine of 20 mg/m² administered as a one hour (1 h) infusion. Also provided are methods of treatment using a solid oral dosage form according to an embodiment of the invention.

9 Claims, 6 Drawing Sheets

COMBINATION DECITABINE AND CEDAZURIDINE SOLID ORAL DOSAGE FORMS

STATEMENT OF PRIORITY

This application is a continuation of and claims priority to U.S. patent application Ser. No. 17/904,536, filed Aug. 18, 2022, which is a 35 U.S.C. § 371 national phase application of PCT Application PCT/US2021/019310 filed Feb. 24, 2021, which claims the benefit of U.S. Provisional Application Ser. No. 62/981,304, filed Feb. 25, 2020, the entire contents of each of which are incorporated by reference herein.

FIELD OF THE INVENTION

The invention relates to solid oral dosage forms that include cedazuridine and decitabine. In particular, the invention relates to solid oral dosage forms that include a fixed dose combination of cedazuridine and decitabine, wherein the dosage forms provide pharmacokinetic and/or pharmacodynamic effects equivalent to those obtained with intravenous decitabine.

BACKGROUND OF THE INVENTION

The enzymes adenosine deaminase (ADA, EC 3.5.4.4) and cytidine deaminase (CDA, EC 3.5.4.5) function to deaminate natural aminopurine and aminopyrimidine nucleosides, respectively, in human and other organisms. They may also convert active nucleoside-based drugs into inactive metabolites. CDA is a component of the pyrimidine salvage pathway. It converts cytidine and deoxycytidine to uridine and deoxyuridine, respectively, by hydrolytic deamination (*Arch. Biochem. Biophys.* 1991, 290, 285-292; *Methods Enzymol.* 1978, 51, 401-407; *Biochem. J.* 1967, 104, 7P). It also deaminates a number of synthetic cytosine analogs which are clinically useful drugs (*Cancer Chemother. Pharmacol.* 1998, 42, 373-378; *Cancer Res.* 1989, 49, 3015-3019; *Antiviral Chem. Chemother.* 1990, 1, 255-262). Conversion of the cytosine compounds to the uridine derivatives usually confers loss of therapeutic activity or addition of side-effects. It has also been shown that cancers that acquire resistance to cytosine analog drugs often overexpress CDA (*Leuk. Res.* 1990, 14, 751-754). Leukemic cells expressing a high level of CDA can manifest resistance to cytosine antimetabolites and thereby limit the antineoplastic activity of such therapeutics (*Biochem. Pharmacol.* 1993, 45, 1857-1861). CDA is also highly expressed in the gut and liver and so may affect the bioavailability of therapeutic cytidine analogs.

Decitabine (5-aza-2'-deoxycytidine), a cytidine analog, is an antineoplastic agent and hypomethylating agent (HMA) for the treatment of myelodysplastic syndromes (MDS), with potential utility for the treatment of acute myelogenous leukemia and chronic myelogenous leukemia as well. Decitabine is not readily bioavailable when administered orally because of rapid inactivation by CDA.

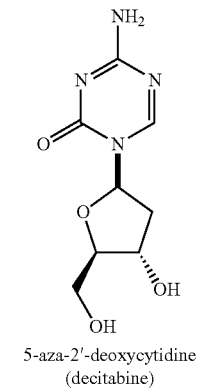

5-aza-2'-deoxycytidine
(decitabine)

Cedazuridine ((4R)-2'-deoxy-2',2'-difluoro-3,4,5,6-tetrahydrouridine; also known as E7727) is a recently developed CDA inhibitor. Cedazuridine and methods of making and/or using thereof are further disclosed in U.S. Pat. Nos. 8,268,800 and 9,834,576, the contents of which are incorporated by reference herein in their entirety.

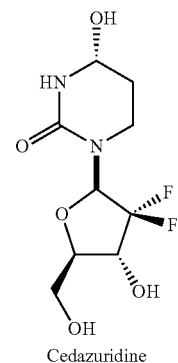

Cedazuridine

Due to decitabine's lack of bioavailability when orally administered, treatment methods using decitabine currently require parenteral injections daily for 5-7 days for several months or even years. An orally bioavailable decitabine dosage form would decrease the burden of monthly, multiple-day, intravenous infusions or subcutaneous injections, which sometimes involve long-distance travel for clinic visits.

SUMMARY OF THE INVENTION

The present invention is based, in part, on the development of solid oral dosage forms of decitabine and cedazuridine, wherein the solid oral dosage form upon daily administration to a subject provides plasma levels of decitabine with a 5-day area under the curve (AUC) for decitabine that is equivalent to the 5-day AUC for a daily intravenous (IV) dose of decitabine of 20 mg/m² administered as a one hour infusion. In some embodiments, upon daily administration of such solid oral dosage form to a subject, the ratio of AUC for decitabine on day 2 versus day 1 is about 1.5:1 to about 2:1.

Another aspect of the invention relates to solid oral dosage forms comprising decitabine and cedazuridine wherein the solid oral dosage forms upon daily administration to a subject provide a pharmacodynamic effect that is equivalent to the pharmacodynamic effect for a daily intravenous dose of decitabine of 20 mg/m² administered as a one hour infusion. In particular embodiments, the pharmacodynamic effect is DNA demethylation.

An additional aspect of the invention relates to methods for treating a disorder in a subject in need thereof, comprising administering to the subject a solid oral dosage form according to an embodiment of the invention, thereby treating cancer in the subject. In some embodiments, the disorder is cancer.

A further aspect of the invention relates to methods for inhibiting degradation of decitabine in a subject in need thereof, comprising administering to the subject a solid oral dosage form according to an embodiment of the invention, thereby inhibiting degradation of the decitabine in the subject.

Another aspect of the invention relates to methods of reducing DNA methylation (e.g., LINE-1 methylation) in a subject in need thereof, comprising administering to the subject a solid oral dosage form according to an embodiment of the invention, thereby reducing DNA methylation in the subject.

An additional aspect of the invention relates to use of a solid oral dosage form according to an embodiment of the invention in methods for treating a disorder, methods for inhibiting degradation of decitabine, and methods of reducing DNA methylation (e.g., LINE-1 methylation).

These and other aspects of the invention are set forth in more detail in the description of the invention below.

BRIEF DESCRIPTION OF THE DRAWINGS

FIG. 5A provides the relative LINE-1 progression for the ASTX727 course and FIG. 5B provides the relative LINE-1 progression for the IV decitabine course.

FIG. 6A provides the relative LINE-1 progression for the IV decitabine course, and FIG. 6B provides the relative LINE-1 progression for the ASTX727 course.

FIG. 8 shows the plasma decitabine $AUC_{0\text{-}24}$ (h·ng/mL) for oral ASTX727 at days 1, 2, and 5, and $AUC_{0\text{-}24}$ (h·ng/mL) for IV decitabine for days 1 and 5.

DETAILED DESCRIPTION OF THE INVENTION

Figure 1:
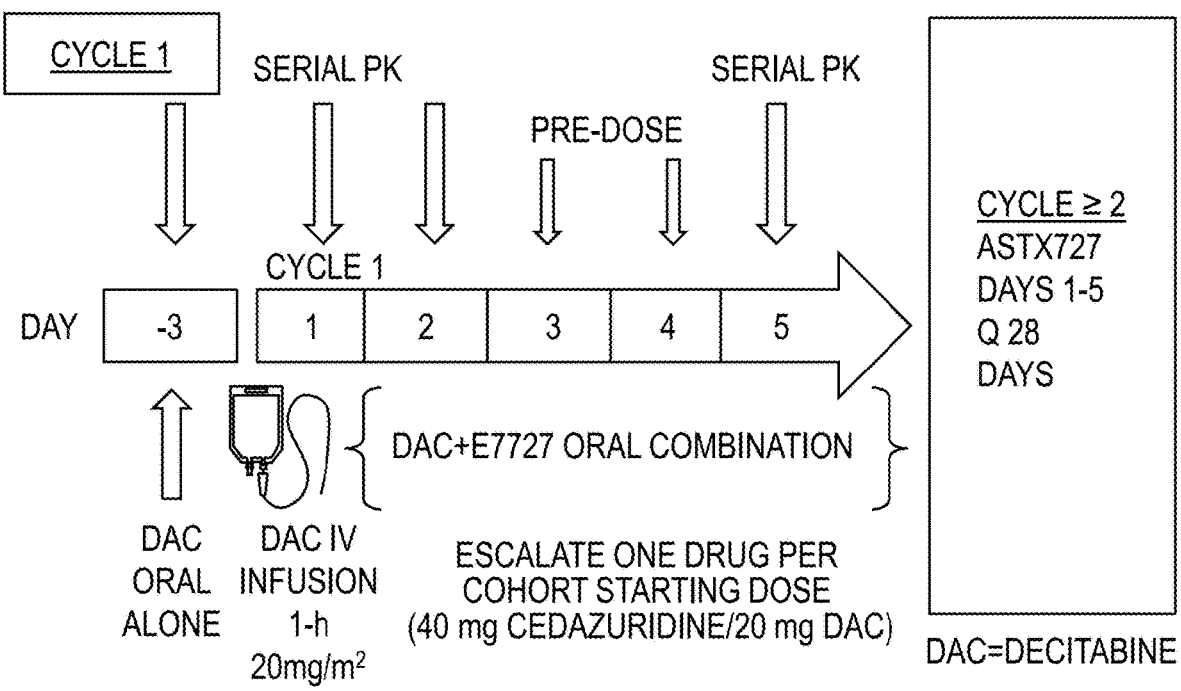
FIG. 1 is a graphic describing a Phase 1 dose escalation study designed to establish the recommended dose of cedazuridine and decitabine.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations, and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention.

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention.

Thus, the term "consisting essentially of" as used herein should not be interpreted as equivalent to "comprising."

"Effective amount" refers to the amount required to produce a desired effect (e.g., enhancing the half-life, bioavailability, or efficacy of a CDA substrate drug, treating cancer in a subject, reducing DNA methylation in a subject, inhibiting cytidine deaminase in a subject, or inhibiting degradation of a CDA substrate drug by cytidine deaminase).

"AUC" refers to the area under the concentration time curve of an active agent such as decitabine.

"Half-life" refers to the period of time required for the concentration or amount of a compound in a subject to be reduced to exactly one-half of a given concentration or amount.

"Pharmaceutically acceptable" refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability, and compatibility with other ingredients.

"Pharmaceutically acceptable salt" refers to an acid or base salt of a compound of the invention, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quaternized with agents including lower alkyl halides such as methyl, ethyl, propyl and butyl chlorides, bromides, and iodides; dialkyl sulfates such as dimethyl, diethyl, dibutyl and diamyl sulfates; long chain halides such as decyl, lauryl, myristyl and stearyl chlorides, bromides, and iodides; and aralkyl halides such as phenethyl bromides.

"Unit dosage form" refers to a physically discrete unit suitable as a unitary dosage for human or other animal subjects. Each unit dosage form may contain a predetermined amount of an active substance (e.g., compound or composition of the invention, CDA substrate drug and/or other therapeutic agent) calculated to produce a desired effect.

"Optional" or "optionally" means that the subsequently described event or circumstance may or may not occur, and that the description includes instances where the event or circumstance occurs and instances in which it does not. For example, an alkyl that is "optionally substituted" encompasses both an alkyl that is unsubstituted and an alkyl that is substituted.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, fifteen-fold, etc.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

"Subject" refers to a cell or tissue, in vitro or in vivo, an animal or a human. An animal or human subject may also be referred to as a "patient."

"Animal" refers to a living organism having sensation and the power of voluntary movement, and which requires for its existence oxygen and organic food.

"Mammal" refers to a warm-blooded vertebrate animal with hair or fur. Examples include without limitation members of the human, equine, porcine, bovine, murine, canine, or feline species.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved. "Treating" in reference to a disease, disorder or condition may refer to: (i) inhibiting a disease, disorder, or condition, e.g., arresting its development; and/or (ii) relieving a disease, disorder, or condition, e.g., causing regression of the clinical symptoms.

"Preventing" in reference to a disease, disorder or condition refers to preventing a disease, disorder, or condition, e.g., causing the clinical symptoms of the disease, disorder, or condition not to develop. As used herein, the term "prevent," "prevents," or "prevention" (and grammatical equivalents thereof) may also refer to a delay in the onset of a disease or disorder or the lessening of symptoms upon onset of the disease or disorder. The terms are not meant to imply complete abolition of disease and encompass any type of prophylactic treatment that reduces the incidence of the condition or delays the onset and/or progression of the condition.

The term "administering" or "administration" of a compound and/or composition of the present invention to a subject includes a route of introducing or delivering to a subject a compound to perform its intended function. For the solid oral dosage forms of the invention, the method of administration is intended to be oral. The pharmacokinetics and pharmacodynamic for the solid oral dosage forms are compared with those obtained by intravenous administration of decitabine, which is typically provided via an infusion. When the infusion is said to be administered over one (1) hour, it is intended to mean that a solution comprising decitabine at the stated concentration is administered over that time period. Administration includes self-administration and the administration by another.

"Cancer" refers to an abnormal growth of cells which tend to proliferate in an uncontrolled way and, in some cases, to metastasize (spread). Specific cancers types include without limitation the cancers identified in Publication No. US 2006/0014949 and the following: cardiac: sarcoma (e.g., such as angiosarcoma, fibrosarcoma, rhabdomyosarcoma, liposarcoma and the like), myxoma, rhabdomyoma, fibroma, lipoma and teratomas; lung: bronchogenic carcinoma (e.g., such as squamous cell, undifferentiated small cell, undifferentiated large cell, adenocarcinoma and the like), alveolar (e.g., such as bronchiolar) carcinoma, bronchial adenoma, sarcoma, lymphoma, chondromatous hamartoma, mesothelioma; gastrointestinal: esophagus (e.g., such as squamous cell carcinoma, adenocarcinoma, leiomyosarcoma, lymphoma and the like), stomach (e.g., such as carcinoma, lymphoma, leiomyosarcoma and the like), pancreas (e.g., such as ductal adenocarcinoma, insulinoma, glucagonoma, gastrinoma, carcinoid tumors, vipoma and the like), small bowel (e.g., such as adenocarcinoma, lymphoma, carcinoid tumors, Kaposi's sarcoma, leiomyoma, hemangioma, lipoma, neurofibroma, fibroma, and the like), large bowel (e.g., such as adenocarcinoma, tubular adenoma, villous adenoma, hamartoma, leiomyoma and the like); genitourinary tract: kidney (e.g., such as adenocarcinoma, Wilm's tumor nephroblastoma, lymphoma, leukemia, and the like), bladder and urethra (e.g., such as squamous cell carcinoma, transitional cell carcinoma, adenocarcinoma and the like), prostate (e.g., such as adenocarcinoma, sarcoma), testis (e.g., such as seminoma, teratoma, embryonal carcinoma, teratocarcinoma, choriocarcinoma, sarcoma, interstitial cell carcinoma, fibroma, fibroadenoma, adenomatoid tumors, lipoma and the like); liver: hepatoma (e.g., hepatocellular carcinoma and the like), cholangiocarcinoma, hepatoblastoma, angiosarcoma, hepatocellular adenoma, hemangioma; bone: osteogenic sarcoma (e.g., such as osteosarcoma and the like), fibrosarcoma, malignant fibrous histiocytoma, chondrosarcoma, Ewing's sarcoma, malignant lymphoma (e.g., such as reticulum cell sarcoma), multiple myeloma, malignant giant cell tumor chordoma, osteochondroma (e.g., such as osteocartilaginous exostoses), benign chondroma, chondroblastoma, chondromyxofibroma, osteoid osteoma and giant cell tumors; nervous system: skull (e.g., such as osteoma, hemangioma, granuloma, xanthoma, osteitis deformans and the like), meninges (e.g., such as meningioma, meningiosarcoma, gliomatosis and the like), brain (e.g., such as astrocytoma, medulloblastoma, glioma, ependymoma, germinoma [pinealoma], glioblastoma multiform, oligodendroglioma, schwannoma, retinoblastoma, congenital tumors and the like), spinal cord (e.g., such as neurofibroma, meningioma, glioma, sarcoma and the like); gynecological: uterus (e.g., such as endometrial carcinoma and the like), cervix (e.g., such as cervical carcinoma, pre-tumor cervical dysplasia and the like), ovaries (e.g., such as ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, and the like), vulva (e.g., such as squamous cell carcinoma, intraepithelial carcinoma, adenocarcinoma, fibrosarcoma, melanoma and the like), vagina (e.g., such as clear cell carcinoma, squamous cell carcinoma, botryoid sarcoma (embryonal rhabdomyosarcoma], fallopian tubes (carcinoma) and the like); hematologic: blood (e.g., such as myeloid leukemia [acute and chronic], acute lymphoblastic leukemia, chronic lymphocytic leukemia, myeloproliferative diseases, multiple myeloma, myelodysplastic syndromes and the like), Hodgkin's disease, non-Hodgkin's lymphoma; skin: malignant melanoma, basal cell carcinoma, squamous cell carcinoma, Kaposi's sarcoma, moles dysplastic nevi, lipoma, angioma, dermatofibroma, keloids, psoriasis and the like; and adrenal glands: neuroblastoma.

Solid Oral Dosage Formulations

The present invention provides solid oral dosage forms comprising decitabine and cedazuridine. The solid oral dosage form is referred to as ASTX727 and marketed as INQOVI® for the treatment of myelodysplastic syndromes. Previously, it has been shown that administering an oral dose of cedazuridine before administering an oral dose of decitabine enhances the exposure of decitabine. However, given the low bioavailability of decitabine and decrease in bioavailability of oral administration versus intravenous administration generally, a solid oral dosage form comprising decitabine and cedazuridine was expected to have a significantly lower bioavailability than intravenous decitabine. Surprisingly, the inventors of the present invention have discovered solid oral dosage forms that upon daily administration to a subject (e.g., a human) provide plasma levels of decitabine with a 5-day area under the curve (AUC) for decitabine that is equivalent to the 5-day AUC for a daily intravenous (IV) dose of decitabine of 20 mg/m$^2$ administered as a one hour infusion. Additionally, the inventors of the present invention have discovered combination decitabine and cedazuridine solid oral dosage forms that have equivalent or improved epigenetic effects (e.g., LINE-1 demethylation, e.g., % F cell expansion) and/or decreased myelosuppressive effects (e.g., neutropenia), relative to those obtained with IV decitabine, in IPSS-low and IPSS-intermediate-1 myelodysplastic syndromes (MDS) cancer patients. As used herein, the term "equivalent" refers to a value that varies by less than 10% from the reference value, e.g., less than 10%, 9%, 8%, 7%, 6%, 5%, 4%, 3%, 2%, or 1%.

As such, provided according to embodiments of the present invention are solid oral dosage forms that include both decitabine and cedazuridine. As used herein, the terms "decitabine" and "cedazuridine" include the compounds themselves and any pharmaceutically acceptable salts thereof. In some embodiments of the invention, provided are solid oral dosage forms comprising decitabine and cedazuridine, wherein the solid oral dosage forms upon daily administration to a subject provide plasma levels of decitabine with a 5-day AUC for decitabine that is equivalent to the 5-day AUC for a daily IV dose of decitabine of 20 mg/m$^2$ administered as a one hour (1 h) infusion. In some embodiments of the invention, upon daily administration to a subject, the ratio of AUC ($AUC_{0-24}$) for decitabine on day 2 versus day 1 is about 1.5:1 to about 2:1, e.g., about 1.5:1 to about 1.8:1, e.g., about 1.7:1 to about 2:1, e.g., about 1.5:1, 1.6:1, 1.7:1, 1.8:1, 1.9:1, or 2:1.

The Primary Endpoint PK Analysis Set is used to calculate decitabine 5-day cumulative $AUC_{0-t}$ exposures after administration of the solid dosage form. The following assumptions are used:

1) Steady state is reached on Day 2 of dosing with the solid dosage form;
2) Based on steady state achievement on Day 2, decitabine $AUC_{0-t}$ from Day 2 and Day 5 is representative of daily $AUC_{0-t}$ on Days 2 through Day 5 in a putative 5-day dosing with the solid dosage form.

Therefore, to calculate total 5-day oral decitabine $AUC_{0-t}$ exposures using PK data from 3 days sequential PK sampling, Day 1 $AUC_{0-t}$ (first solid dosage form dose) is added to (Day 2 $AUC_{0-t}$+Day 5 $AUC_{0-t}$)×2. If $AUC_{0-t}$ on Day 2 is not available, it is replaced by $AUC_{0-t}$ on Day 5; the converse is also true.

To calculate decitabine 5-day $AUC_{0-t}$ exposures after IV decitabine, (Day 1 $AUC_{0-t}$+Day 5 $AUC_{0-t}$)/2 is multiplied by 5, based on DACOGEN® prescribing information (DACOGEN® Prescribing Information 2014) that there was no accumulation on Day 5 vs Day 1 for a 5-day infusion. If $AUC_{0-t}$ on Day 1 is not available, it is replaced by $AUC_{0-t}$ on Day 5; the converse is also true. Note that t=24 hrs, so $AUC_{0-t}$ is $AUC_{0-24}$.

In some embodiments of the present invention, the solid oral dosage form upon daily administration to a subject provides a pharmacodynamic effect that is equivalent to the pharmacodynamic effect for a daily intravenous dose of decitabine of 20 mg/m$^2$ administered as a one hour (1 h)

infusion. The type of pharmacodynamic effect includes any effect now known or later discovered. In particular embodiments, the pharmacodynamic effect is DNA demethylation.

The pharmaceutical compositions (e.g., compound, composition, drug, and/or therapeutic agent) comprising decitabine and cedazuridine are provided as a solid oral dosage form, meaning that the pharmaceutical compositions are in solid form and are formulated for oral administration. Any suitable solid oral dosage form may be used. Examples of solid oral dosage forms according to embodiments of the invention include tablets (for example, those targeted for buccal, sublingual, and systemic absorption), caplets, boluses, powders, granules, pastes for application to the tongue, capsules including hard gelatin capsules and soft gelatin capsules, mouth sprays, troches, lozenges, and pellets. The pharmaceutical compositions may be formulated for immediate, sustained, or controlled release.

Pharmaceutical compositions of the invention can be prepared using known materials and techniques, which may include but are not limited to mixing and/or blending decitabine and cedazuridine with the pharmaceutically acceptable excipients.

In some embodiments of the invention, the solid oral dosage form comprises decitabine and cedazuridine in a weight ratio in a range of about 30:100 to about 40:100, e.g., about 35:100.

In some embodiments of the invention, the solid oral dosage form is a unit dosage form that comprises about 35 mg decitabine. In some embodiments of the invention, the solid oral dosage form is unit dosage form that comprises about 100 mg of cedazuridine. Furthermore, in some embodiments, the solid oral dosage form is a unit dosage form that comprises about 35 mg decitabine and about 100 mg of cedazuridine. In some embodiments of the invention, the unit dosage form comprises about 35 mg decitabine and about 100 mg of cedazuridine and at least one pharmaceutically acceptable excipient.

"Pharmaceutically acceptable excipient" can mean any substance, not itself a therapeutic agent, used as a carrier, diluent, adjuvant, binder, and/or vehicle for delivery of a therapeutic agent to a subject, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa (e.g., 20th Ed., 2000), and Handbook of Pharmaceutical Excipients, American Pharmaceutical Association, Washington, D.C., (e.g., 1st, 2nd and 3rd Eds., 1986, 1994 and 2000, respectively). As will be known to those skilled in the art, excipients may provide a variety of functions and may be described as, e.g., wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose (hypromellose), and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Examples of diluents include lactose, lactose monohydrate, cellulose, microcrystalline cellulose, sorbitol, dibasic calcium phosphate dehydrate, and calcium sulfate dehydrate. Examples of binders include gelatin, glucose, lactose, cellulose, methyl cellulose, ethyl cellulose, hydroxypropyl methyl cellulose (hypromellose), hydroxypropyl cellulose, starch, poly vinyl pyrrolidone, sodium alginate, carboxymethylcellulose, and acacia. Examples of disintegrants include croscarmellose sodium, crospovidone, sodium starch glycollate, and starch. Examples of glidants include colloidal silicon dioxide, cornstarch, and talc. Examples of lubricants include stearic acid, magnesium stearate, calcium stearate, talc, paraffin, sodium lauryl sulphate, sodium benzoate, and polyethylene glycol.

In some embodiments, the solid oral dosage form includes one or more of a diluent, binder, disintegrant, glidant, and lubricant. In some embodiments, the solid oral dosage form includes a diluent, binder, disintegrant, glidant, and lubricant. In particular embodiments of the invention, the solid oral dosage form includes the following excipients: lactose monohydrate as a diluent; hydroxypropyl methylcellulose as a binder; croscarmellose sodium as a disintegrant; colloidal silicon dioxide as a glidant; and magnesium stearate as a lubricant. In some embodiments of the invention, such components are formed into a tablet. In some embodiments, the tablet is an immediate release tablet. Additionally, in particular embodiments, the tablet is coated with a film, which may be colored. Any pharmaceutically acceptable coating may be used but in some embodiments, the tablet is coated with an OPADRY® coating.

In some embodiments, the cedazuridine is present in the solid oral dosage form in an amount of about 17-22% w/w, e.g., about 17.0, 17.2, 17.4, 17.6, 17.8, 18.0, 18.2, 18.4, 18.6, 18.8, 19.0, 19.2, 19.4, 19.6, 19.8, 20.0, 20.2, 20.4, 20.6, 20.8, 21.0, 21.2, 21.4, 21.6, 21.8, or 22.0% w/w or any range therein, e.g., about 19.42% w/w.

In some embodiments, the decitabine is present in the solid oral dosage form in an amount of about 4-8% w/w, e.g., about 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, or 8.0% w/w or any range therein, e.g., about 6.8% w/w.

In some embodiments, the diluent (e.g., lactose monohydrate) is present in the solid oral dosage form in an amount of about 55-70% w/w, e.g., about 55, 56, 57, 58, 59, 60, 61, 62, 63, 64, 65, 66, 67, 68, 69, or 70% w/w or any range therein, e.g., about 62.62% w/w.

In some embodiments, the binder (e.g., hypromellose) is present in the solid oral dosage form in an amount of about 1-3% w/w, e.g., about 1.0, 1.2, 1.4, 1.6, 1.8, 2.0, 2.2, 2.4, 2.6, 2.8, or 3.0% w/w or any range therein, e.g., about 1.94% w/w.

In some embodiments, the disintegrant (e.g., croscarmellose sodium) is present in the solid oral dosage form in an amount of about 3-7% w/w, e.g., about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, or 7.0% w/w or any range therein, e.g., about 4.85% w/w.

In some embodiments, the glidant (e.g., colloidal silicon dioxide) is present in the solid oral dosage form in an amount of about 0.5-2% w/w, e.g., about 0.5, 0.6, 0.7, 0.8, 0.9, 1.0. 1.1, 1.2, 1.3, 1.4, 1.5, 1.6, 1.7, 1.8, 1.9, or 2.0% w/w or any range therein, e.g., about 0.97% w/w.

In some embodiments, the lubricant (e.g., magnesium stearate) is present in the solid oral dosage form in an amount of about 0.1-2% w/w, e.g., about 0.1, 0.2, 0.3, 0.4, 0.5, 0.6, 0.7, 0.8, 0.9, 1.0. 1.1, 1.2, 1.3, 1.4, 1.5, 1.6, 1.7, 1.8, 1.9, or 2.0% w/w or any range therein, e.g., about 0.49% w/w.

In some embodiments, the solid oral dosage form comprises the components listed in Table 2.

TABLE 1

| Component | Function | Composition (% w/w) |
|---|---|---|
| Cedazuridine | Active | 17-22 |
| Decitabine | Active | 4-8 |
| Lactose monohydrate | Diluent | 55-70 |
| Hypromellose | Binder | 1-3 |
| Croscarmellose sodium | Disintegrant | 3-7 |
| Colloidal silicon dioxide | Glidant | 0.5-2 |
| Magnesium stearate | Lubricant | 0.1-2 |

In some embodiments, the solid oral dosage form comprises the components listed in Table 2.

TABLE 2

| Component | Function | Composition (% w/w) |
|---|---|---|
| Cedazuridine | Active | 19.42 |
| Decitabine | Active | 6.80 |
| Lactose monohydrate | Diluent | 62.62 |
| Hypromellose | Binder | 1.94 |
| Croscarmellose sodium | Disintegrant | 4.85 |
| Colloidal silicon dioxide | Glidant | 0.97 |
| Magnesium stearate | Lubricant | 0.49 |
| Total Core Tablet | | 97.09 |
| Coating | Film Coat | 2.91 |
| Total Coated Tablet | | 100.0 |

Another aspect of the present invention relates to a unit dosage form and a kit comprising at least one unit dosage form, which unit dosage form comprises decitabine and cedazuridine. In some embodiments, the kit provides unit dosage forms comprising cedazuridine and decitabine wherein upon daily administration to a subject (e.g., a human), the plasma level 5-day AUC for decitabine is equivalent to the 5-day AUC for a daily IV dose of decitabine of 20 mg/m$^2$ administered as a one hour (1 h) infusion. Alternatively or additionally, in some embodiments, provided are kits comprising unit dosage forms including decitabine and cedazuridine wherein upon daily administration to a subject (e.g., human) provides a pharmacodynamic effect that is equivalent to the pharmacodynamic effect for a daily intravenous dose of decitabine of 20 mg/m$^2$ administered as a one hour (1 h) infusion. As such, the kit may include 1, 2, 3, 4, 5, or more solid oral dosage forms according to an embodiment of the invention. In some embodiments, the kit comprises 5, 6, or 7 unit dosage tablets comprising about 35 mg decitabine and about 100 mg of cedazuridine and at least one pharmaceutically acceptable excipient.

The kit may further comprise a container and/or a package suitable for commercial sale. The container can be in any conventional shape or form known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box. In some embodiments, the container is a bottle, e.g., a 30-cc white high-density polyethylene bottles containing unit dosage forms (e.g., about 5 unit dosage forms). The bottle may further contain desiccant, e.g., silica desiccant canisters. In some embodiments, the container is a blister pack, e.g., formed by aluminum foil on foil lidding containing one tablet per cavity. The blister packs may be present in a carton.

The kit may further comprise information. The information may be provided on a readable medium. The readable medium may comprise a label. The information may be directed towards a physician, pharmacist, or patient. The information may indicate that the unit dosage form may cause one or more adverse effects. The information may comprise instructions for administering the unit dosage form, such as in a manner described herein. These instructions may be provided in a variety of ways.

The information can be associated with the container, for example, by being: written on a label (e.g., the prescription label or a separate label) adhesively affixed to a container; included inside a container as a written package insert; applied directly to the container such as being printed on the wall of a box or blister pack; or attached as by being tied or taped, for example as an instructional card affixed to the neck of a bottle via a string, cord or other line, lanyard or tether type device.

Methods Using Solid Oral Dosage Forms of the Invention

Provided according to embodiments of the invention are methods of administering to a subject a solid oral dosage form comprising cedazuridine and decitabine. In particular embodiments, provided are methods of administering to a subject a solid oral dosage form comprising cedazuridine and decitabine, wherein the solid oral dosage form upon daily administration to a subject (e.g., a human) provides plasma levels of decitabine with a 5-day AUC for decitabine that is equivalent to the 5-day AUC for a daily IV dose of decitabine of 20 mg/m$^2$ administered as a one hour (1 h) infusion. In some embodiments, upon daily administration to a subject, the ratio of AUC for decitabine on day 2 versus day 1 is about 1.5:1 to about 2:1. In some embodiments of the present invention, the methods comprise administering to the subject a solid oral dosage form comprising decitabine and cedazuridine, wherein the solid oral dosage form upon daily administration to a subject provides a pharmacodynamic effect that is equivalent to the pharmacodynamic effect for a daily intravenous dose of decitabine of 20 mg/m$^2$ administered as a one hour (1 h) infusion. In particular embodiments, the pharmacodynamic effect is DNA demethylation. The solid oral dosage form used may be any solid oral dosage form described herein.

Furthermore, provided are methods of treating a disorder that is treatable with decitabine in a subject in need thereof, comprising administering to the subject a solid oral dosage form according to an embodiment of the invention, thereby treating the disorder in the subject. In some embodiments, the disorder that is treatable with decitabine is a hyperproliferative disorder, e.g., cancer. The methods can be used to treat any cancer which decitabine is known or later discovered to be effective in treating. In particular embodiments, the disorder is a cancer selected from hematological cancers and solid cancers. Examples of hematological cancers includes myelodysplastic syndromes (MDS), leukemia (e.g., acute lymphocytic leukemia (ALL), acute myelogenous leukemia (AML), chronic myelogenous leukemia (CML), myeloproliferative neoplasms (MPN), or chronic myelomonocytic leukemia (CMML)), and lymphoma (e.g., Hodgkin's Lymphoma, Non-Hodgkin lymphoma, or T-cell lymphoma). In some embodiments, the solid cancer includes pancreatic cancer, ovarian cancer, peritoneal cancer, non-small cell lung cancer, breast cancer, neuroectodermal tumors and/or sarcomas.

In some embodiments, the present invention provides a method for treating a hyperproliferative disorder, e.g., cancer, wherein the cancer is MDS. MDS is a group of cancer disorders with shared improper maturation of bone marrow derived blood cells, and symptoms can vary. The International Prognostic Scoring System (IPSS) scores MDS severity into several risk groups based on patient hemoglobin levels, absolute neutrophil count (ANC), platelet count, and percent bone marrow blasts. Risk groups include "low", "intermediate-1", "intermediate-2", and "high". Other risk group scoring methodologies exist such as the Revised IPSS (IPSS-R) and the WHO classification-based Prognostic Scoring System (WPSS), as described in the NCCN Guidelines for Patients, Myelodysplastic Syndromes, 2018. Methods of the present invention may be used to treat a hyperproliferative disorder, e.g., cancer in a subject (e.g., a human patient) diagnosed with any risk group of MDS based on any scoring methodology. In some embodiments, a subject in need of the present invention may include a subject diagnosed with lower risk MDS (defined as IPSS low and/or intermediate-1).

In some embodiments of the invention, provided are methods for inhibiting degradation of decitabine in a subject in need thereof, comprising administering to the subject a solid oral dosage according to an embodiment of the invention, thereby inhibiting degradation of decitabine in the subject.

In some embodiments, the present invention provides a method of reducing DNA methylation in a subject in need thereof, comprising administering to the subject a solid oral dosage form according to an embodiment of the invention, thereby reducing DNA methylation in the subject (e.g., thereby enabling reduction in DNA methylation by the CDA substrate drug). The DNA methylation may be reduced relative to the methylation level in the subject prior to treatment. In some embodiments, the administering reduces DNA methylation of LINE-1. LINE-1 is a long interspersed nuclear element found in human DNA (e.g., the subject) known in the art, and its methylation levels can be measured using standard techniques in the art to determine genetic effects of hypomethylating agents such as CDA substrate drugs (e.g., decitabine).

The administering to a subject in need thereof of a solid oral dosage form according to an embodiment of the invention has been shown by the inventors of the present invention to provide multiple beneficial responses to the subject. For example, in some embodiments, the administering reduces DNA methylation in the subject by at least 5% (e.g., at least 5, 6, 7, 8, 9, 10, 11, 12, 13, 14, or 15% or more or any value or range therein) as compared to a control measurement, e.g., as compared to DNA methylation in the subject prior to the administering (e.g., subject "baseline" DNA methylation). DNA methylation in the subject may be quantitatively and/or qualitatively evaluated by any standard technique in the art, e.g., as measured by a marker of relative global methylation as compared to a control, e.g., as measured by LINE-1 methylation as compared to a control. For example, in some embodiments, the administering reduces LINE-1 methylation in the subject by at least 5% (e.g., at least 5, 6, 7, 8, 9, 10, 11, 12, 13, 14, or 15% or more) as compared to a control measurement, e.g., as compared to LINE-1 methylation in the subject prior to the administering (e.g., subject baseline LINE-1 methylation). For example, in some embodiments, the administering may reduce LINE-1 methylation in the subject by at least 5%, at least 8%, at least 10% or at least 15% or more. In some embodiments, the administering may reduce LINE-1 methylation in the subject by about 5% to about 20%, about 6% to about 15%, or by about 8% to about 10%.

In some embodiments, the administering may reduce absolute neutrophil count (ANC) in the subject to less than $0.5 \times 10^9$ cells/L of blood for no more than two weeks (e.g., no more than 14, 13, 12, 11, 10, 9, 8, 7, 6, 5, 4, 3, or 2 consecutive days or any value or range therein) following a 28-day cycle. In some embodiments, the administering reduces absolute neutrophil count (ANC) in the subject to less than $0.5 \times 10^9$ cells/L of blood for no more than two weeks (e.g., more than two, three, four, five, six weeks etc.) during treatment (e.g., between multiple, repeated 28-day cycles).

In some embodiments, the administering expands hemoglobin F-expressing cells (i.e., F cells) by at least 5% (e.g., at least 5, 6, 7, 8, 9, 10, 15, 20, 25, or 30% or more), optionally as measured by % F cells/erythrocytes per sample (e.g., in a patient blood sample) as compared to a "baseline" control % F cells/erythrocytes (e.g., as compared to % F cells/erythrocytes of the patient prior to treatment, e.g., as compared to the average % F cells/erythrocytes of a patient population not undergoing treatment (e.g., a healthy patient population)). For example, in some embodiments, the administering may expand % F cells in the subject by at least 5%, at least 8%, at least 10%, at least 15%, or at least 23% or more as compared to a baseline control. In some embodiments, the administering may expand % F cells in the subject by about 5% to about 30%, about 6% to about 24%, or by about 8% to about 20% as compared to a baseline control.

In some embodiments, the administering expands F cells to a total amount of at least 10% to at least 30% or more of total erythrocytes (e.g., at least 15%, 16%, 17%, 18%, 19%, 20%, 21%, 22%, 23%, 24%, 25%, 26%, 27%, 28%, 29%, or 30% or more F cells/erythrocytes or any value or range therein) per sample (e.g., in a patient blood sample). For example, in some embodiments, the administering may expand F cells to a total amount of at least 15%, at least 20%, at least 23%, at least 35% or more of total erythrocytes in a sample. In some embodiments, the administering may expand F cells to a total amount of about 15% to about 30%, about 18% to about 25%, or about 15% to about 35%, of total erythrocytes in a sample.

In some embodiments of the methods of the present invention, the subject may be a mammal. In some embodiments of the methods of the present invention, the subject may be a human.

Any administration regimen well known to those skilled in the art for regulating the timing and sequence of drug delivery can be used and repeated as necessary to effect treatment in the methods of the invention. For example, the solid oral dosage forms of the invention may be administered 1, 2, 3, or 4 times daily, by a single dose, multiple discrete doses, or continuous infusion. In particular embodiments, the solid oral dosage form is administered once daily.

In some embodiments of the invention, the administering of solid oral dosage forms according to an embodiment of the invention may be performed about 1 day to about 28 days per 28-day cycle (e.g., about 1, 2, 3, 4, 5, 6, 7, 8, 9, 10, 11, 12, 13, 14, 15, 16, 17, 18, 19, 20, 21, 22, 23, 24, 25, 26, 27, or 28 days per 28-day cycle). In particular embodiments, the administering of solid oral dosage forms is performed once daily for five days (e.g., 5 consecutive days) per 28-day cycle. In some embodiments, the administering of solid oral dosage forms according to the embodiment of the invention may be performed on consecutive days per 28-day cycle. For example, solid oral dosage forms according to the embodiment of the invention may be administered on 5 consecutive days. In some embodiments, solid oral dosage forms according to the embodiment of the invention may be administered on any 3 consecutive days (e.g., on a Monday, Tuesday, and a Wednesday "MTW"; on a Tuesday, Wednesday, and a Thursday "TWTh"; on a Wednesday, Thursday, and a Friday "WThF"; on a Thursday, Friday, and Saturday "ThFS"; on a Friday, Saturday, and a Sunday "FSS"; on a Saturday, Sunday, and a Monday "SSM"; and/or on a Sunday, Monday, and a Tuesday "SMT", etc.). In some embodiments, the administering of solid oral dosage forms according to an embodiment of the invention may be performed on 5 consecutive days (e.g., MTWThF or any other combination of 5 consecutive days), on 7 consecutive days (MTWThFSS or any other combination of 7 consecutive days), on 14 consecutive days (e.g., two consecutive weeks); 21 consecutive days (e.g., three consecutive weeks), and/or on 28 consecutive days (e.g., four consecutive weeks) per 28-day cycle. The consecutive day treatments may be repeated one or more times per 28-day cycle, e.g., every week, every other week.

In some embodiments, the administering of solid oral dosage forms according to an embodiment of the invention may be performed on non-consecutive days per 28-day cycle, e.g., for 1, 2, 3, 4, 5, 6, 7, 8, 9, 10, 11, 12, 13, 14, 15, 16, 17, 18, 19, 20, 21, 22, 23, 24, 25, 26, or 27 or more non-consecutive days. Non-consecutive days may comprise a schedule of every-other day, (e.g., MWF), every two days, every three days, every four days, every five days, every six days, every seven days, etc. in a 28-day cycle. Non-consecutive days may comprise administering for a number of consecutive days (e.g., "on"), followed by a number of days without administering (e.g., "off"), followed by administering for a number of consecutive days (e.g., "on"), etc., within a 28-day cycle. For example, in some embodiments, the administering may be performed on 2 non-consecutive days (e.g., every Monday and Friday or any other combination of 2 non-consecutive days). In some embodiments, the administering may be performed on 3 non-consecutive days (e.g., MWF or any other combination of 3 non-consecutive days). The non-consecutive day treatments may be repeated one or more times per 28-day cycle, e.g., every week, every other week.

In some embodiments, a time period of 0 to 31 days or more (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more) may pass between multiple 28-day treatment cycles of the present invention. The time period of no treatment may be desirable to allow a subject (e.g., a human patient) of the present invention to have adequate health to continue treatment. The time period between treatment cycles can be determined by a physician using standard techniques in the art and may be determined individually on a per-subject basis, for example, as based on adequate blood count, e.g., adequate lack of neutropenia (e.g., absolute neutrophil count (ANC) in the subject of at least or greater than $0.5 \times 10^9$ cells/L), and may be adjusted over the course of treatment based on the judgement of the administering physician. In some embodiments, the time period between treatment cycles may be minimal, e.g., no time period, e.g., immediately starting on the next 28-day time period. In some embodiments, the time period between treatment cycles may be 1 week, 2 weeks, 3 weeks, 4 weeks, 5 weeks, 6 weeks, or more.

In some embodiments, the administering may be performed, e.g., for 10 total days per 28-day cycle, wherein the 10 days of administering comprise 5 consecutive days administering (e.g., 5 days "on"), followed by 2 consecutive days without administering (e.g., 2 days "off"), followed by 5 consecutive days administering (e.g., 5 days "on"), per 28-day cycle. In some embodiments, the administering may be performed, e.g., for 14 total days, wherein the 14 days of administering comprise 7 days "on" followed by 7 days "off" followed by 7 days "on", per 28-day cycle. In some embodiments, the administering may be performed, e.g., for 9 total days, wherein the 9 days of administering comprise 3 consecutive days "on" followed by 4 consecutive days "off", followed by 3 consecutive days "on" followed by 4 consecutive days "off", followed by 3 consecutive days "on", per 28-day cycle. In some embodiments, the administering may be performed, e.g., for 9 total days, wherein the 9 days of administering comprise 3 non-consecutive days "on" (e.g., MWF), followed by 1 day "off", followed by 3 non-consecutive days "on" (e.g., MWF), followed by 1 day "off", followed by 3 non-consecutive days "on", per 28-day cycle.

In some embodiments, the administering a solid oral dosage form according to an embodiment of the invention may be performed for one or more weeks per 28-day cycle, e.g., one week, two weeks, three weeks, or four weeks per 28-day cycle. The weeks may be consecutive and/or non-consecutive.

The administration regimen may include pretreatment and/or co-administration with at least one additional therapeutic agent. In such case, the solid oral dosage form comprising decitabine and cedazuridine may be administered with the at least one additional therapeutic agent simultaneously, separately, or sequentially. The additional therapeutic agent may also be included within the solid oral dosage form.

Examples of a chemotherapeutic agent include without limitation: alkylating agents (e.g., which may include doxorubicin, cyclophosphamide, estramustine, carmustine, mitomycin, bleomycin and the like); antimetabolites (e.g., which may include 5-Fluoro-Uracil, capecitabine, gemcitabine, nelarabine, fludarabine, methotrexate and the like); platinating agents (e.g., which may include cisplatin, oxaliplatin, carboplatin and the like); topoisomerase inhibitors (e.g., which may include topotecan, irinotecan, etoposide and the like); tubulin agents (e.g., which may include paclitaxel, docetaxel, vinorelbine, vinblastine, vincristine, other taxanes, epothilones, and the like); signaling inhibitors (e.g., kinase inhibitors, antibodies, farnesyltransferase inhibitors, and the like); and other chemotherapeutic agents (e.g., tamoxifen, anti-mitotic agents such as polo-like kinase inhibitors or aurora kinase inhibitors, and the like).

In some embodiments, the present invention contemplates about 35 mg per daily dose of decitabine, and so, for example, for a five-day dosing schedule, a cumulative dose on the order of about 175 mg cumulative per 28-day cycle of treatment of decitabine is contemplated. Dose levels, mode of administration, and administration regimen may be modified by those skilled in the art using known techniques as judged necessary for the subject (e.g., the patient).

In some embodiments, the present invention contemplates about 100 mg per daily dose of cedazuridine, and so for a five-day dosing schedule, a cumulative dose on the order of about 500 mg cumulative per 28-day cycle of treatment is contemplated. Dose levels, mode of administration, and administration regimen may be modified by those skilled in the art using known techniques as judged necessary for the subject (e.g., the patient).

In some embodiments, the methods of the present invention can be carried by administering cedazuridine and decitabine separately (e.g., in separate dosage forms) in the same amounts and/or ratios as found in the solid oral dosage forms of the invention and using the same administration regimens.

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

Having described the present invention, the same will be explained in greater detail in the following examples, which are included herein for illustration purposes only, and which are not intended to be limiting to the invention.

EXAMPLES

Example 1: ASTX727 Phase 1 Study

The ASTX727 Phase 1 study was a dose escalation designed to establish the recommended doses of cedazuridine and decitabine likely to achieve AUC equivalence with standard dose decitabine IV (decitabine 20 mg/m$^2$ IV). FIG. 1 provides an overview of the study design. In Cycle 1, each patient received a cohort-defined dose of oral decitabine on day −3, a 1-h intravenous infusion of decitabine 20 mg/m$^2$ on day 1, and cohort-defined doses of oral decitabine plus cedazuridine on days 2-5. In Cycles 2 and beyond, the oral decitabine and cedazuridine were given on days 1-5. The dose of cedazuridine was escalated first and decitabine was escalated once CDA inhibition by cedazuridine approached the maximum effect. Only one drug was escalated per cohort. Fixed doses were given without adjustment for bodyweight or body surface area. Days −3, 1, 2, and 5 for decitabine included a full-day pharmacokinetic analysis. The starting dose was 20 mg for oral decitabine and 40 mg for cedazuridine (a human equivalent dose with approximately 100 times greater safety margin than the no-observed adverse effect level in cynomolgus monkeys). Escalation of each drug was performed if mean decitabine AUC of the oral drug was less than 90% of that for IV decitabine in the cohort and if no dose-limiting toxicity was observed. Dose-limiting toxicity was defined as a grade 4 hematologic toxicity or grade 3 lasting more than 14 days and unrelated to the underlying disease. Once the decitabine AUC target range set as the primary endpoint and established with IV decitabine was reached at a dose deemed to be safe, the cohort that most closely approximated IV decitabine exposure was expanded to 18 evaluable patients. Dose escalation for patients who previously received a lower dose was allowed at the discretion of the investigator if the patient had tolerated the originally assigned doses.

The pharmacokinetic profile of decitabine was characterized through analysis of plasma treated with EDTA (edetic acid) by validated liquid chromatography-tandem mass spectrometry, with tetrahydrouridine (Santa Cruz Biotechnology, Dallas, TX) for stabilization and with a linear assay range of 0.5-100 ng/mL for decitabine. Serial plasma samples (from before dose administration until 24 h after administration) were collected on days −3, 1, 2, and 5 (also immediately before dose administration on days 3 and 4) during the first cycle. Specifically, pharmacokinetic samples were obtained before dose administration and 0.25 h, 0.5 h, 1.0 h (for IV only 1.083 h), 1.5 h, 2 h, 3 h, 4 h, 6 h, 8 h, and 24 h after the dose.

Patients could discontinue treatment or be removed from the study because of disease progression, unacceptable toxicity, patient request, withdrawal of consent, or investigator discretion due to lack of benefit.

Figure 2:
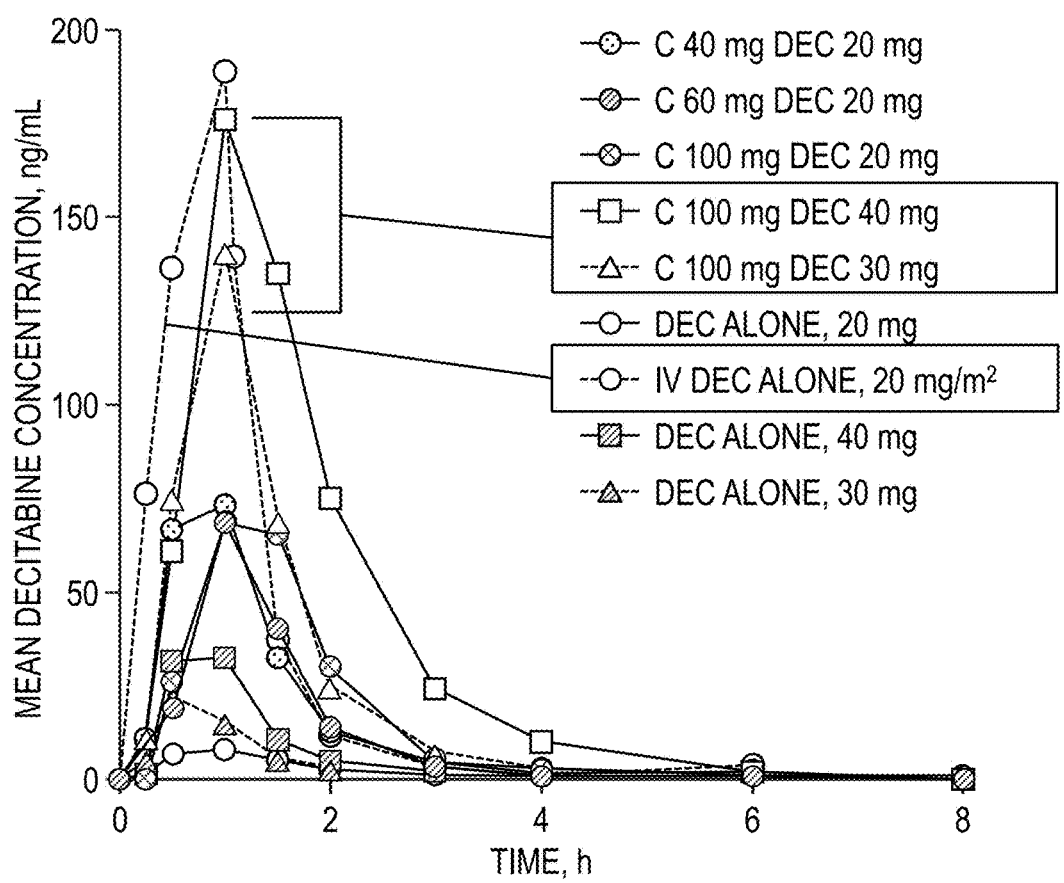
FIG. 2 is a graph of mean decitabine concentration (ng/mL) over time (h) for several dosing regimens in the Phase 1 study described in FIG. 1.

The results of the Phase 1 study are shown in Table 3 and in FIG. 2.

TABLE 3

| | | | | Phase 1 Dose Escalation AUC | | | | | | |
|---|---|---|---|---|---|---|---|---|---|---|
| | | | | $AUC_{0-t}$ by day (h · ng/ml) Geometric Mean (gCV %) | | | | | 5-days Total $AUC_{0-t}$ | |
| | Oral Dose (mg)$^a$ | | | D −3 | D2 | D5 | | | IV | % of AUC |
| Cohort | DEC | CED | N | (DEC alone) | (ASTX727) | (ASTX727) | IV D1 | Oral | (N = 41) | (Oral/IV) |
| 1 | 20 | 40 | 6 | 10.7 (108) | 42.8 (136) | 70.3 (86) | 159 (53) | 324 | | 40 |
| | | | 5$^b$ | 7.90 (58) | 29.0 (45) | 53.6 (40) | 138 (41) | 243 | | 30 |
| 2 | 20 | 60 | 6 | 7.49 (52) | 30.5 (62) | 68.9 (44) | 170 (39) | 306 | 821$^d$ | 37 |
| 3 | 20 | 100 | 6 | 7.90 (147) | 53.5 (44) | 94.8 (46) | 192 (47) | 433 | | 53 |

TABLE 3-continued

Phase 1 Dose Escalation AUC

| Oral Dose (mg)[a] | | | | $AUC_{0-t}$ by day (h · ng/ml) Geometric Mean (gCV %) | | | | 5-days Total $AUC_{0-t}$ | |
|---|---|---|---|---|---|---|---|---|---|
| Cohort | DEC | CED | N | D −3 (DEC alone) | D2 (ASTX727) | D5 (ASTX727) | IV D1 | IV Oral (N = 41) | % of AUC (Oral/IV) |
| 4 | 40 | 100 | 6 | 29.8 (100) | 167 (45) | 221 (74) | 153 (50) | 1050 | 128 |
| 5 | 30 | 100 | 19[c] | 15.3 (92) | 81.7 (59) | 146 (50) | 166 (41) | 667 | 81 |

CED = cedazuridine;
DEC = decitabine;
gCV % = geometric coefficient of variation
[a] Oral dosing was not body weight or body surface area adjusted. IV dose was 20 mg/m² in all cohorts
[b] One subject in Cohort 1 was excluded as an extreme outlier
[c] IV data from 18 patients, one patient was excluded as an extreme outlier
[d] Geometric mean for total 5-day IV $AUC_{0-t}$ calculated for the total IV population (N = 41)

In FIG. 2, the two highlighted curves show the exposures from cedazuridine 100 mg and oral decitabine at 30 and 40 mg (Cohort 4 and 5 in Table 3). At these doses, the oral decitabine exposure was between 81% and 128% of the IV decitabine exposure. Based on this, a middle dose of decitabine between 30 and 40 mg, which is 35 mg, was predicted to be the closest match with the IV.

Example 2: ASTX727 Phase 2 Study Dose Confirmation

Figure 3:
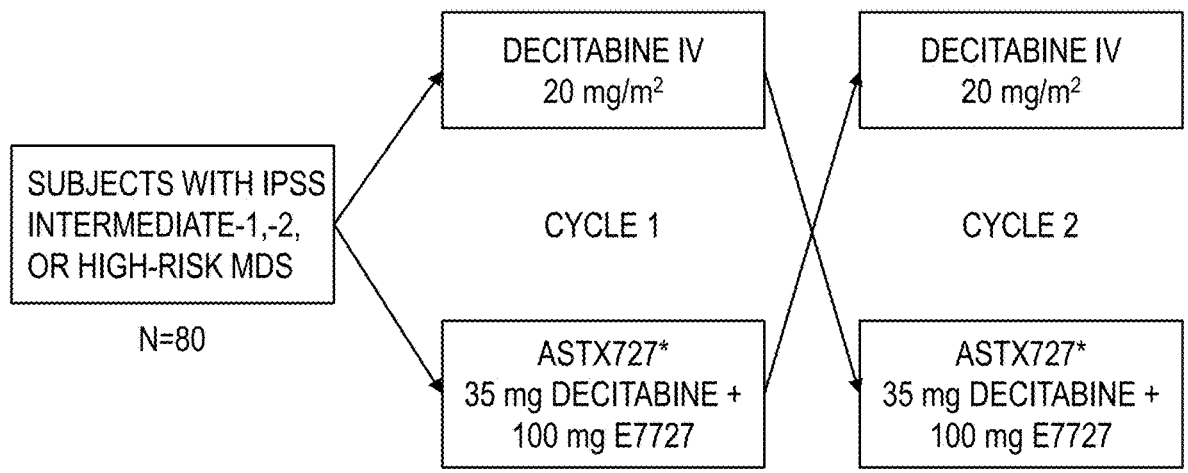
FIG. 3 is a graphic describing a Phase 2 randomized cross over study designed to confirm the dosing of cedazuridine and decitabine identified in the Phase 1 study of FIG. 1.

The ASTX727 Phase 2 study was a randomized cross over design of decitabine 20 mg/m² IV daily (for 5 days) vs. oral decitabine/cedazuridine once daily (for 5 days) in Cycle 1 with patients crossing over to the other drug in Cycle 2 (See FIG. 3). From Cycle 3 onward, all patients continued on oral decitabine/cedazuridine once daily (for 5 days), each cycle every 28 days, until progression.

The baseline characteristics for the patients in Phase 2 are shown in Table 4.

TABLE 4

Phase 2 Patients Baseline Characteristics

| Characteristic | Sequence A (N = 41) ASTX727 → DEC IV | Sequence B (N = 39) DEC IV → ASTX727 |
|---|---|---|
| Median Age (min-max) | 71 (32, 90) Years | 71 (41, 86) Years |
| Sex Male/Female % | 78/22% | 74/26% |
| Median Weight (min-max) | 78.8 (40-122) Kg | 86.2 (42-118) Kg |
| Median BSA | 1.96 (1.3-2.4) m² | 2.05 (1.3-2.4) m² |
| ECOG PC | | |
| 0-1 | 93% | 90% |
| 2 | 7% | 10% |
| IPSS | | |
| Intermediate-1 | 46% | 41% |
| Intermediate-2 or High Risk | 34% | 36% |
| CMML | 20% | 23% |
| Median Hemoglobin (min-max) | 8.75 (7.1-14.9) g/dl | 9.25 (6.8-13.9) g/dl |
| Median Neutrophils (min-max) | 0.94 (0.03-73.6) 10⁹/L | 0.76 (0.06-63.4) 10⁹/L |
| Median Platelets (min-max) | 58.5 (2-523) 10⁹/L | 60.0 (8-569) 10⁹/L |
| RBCs Transfusion Dependence | 48.8% | 46.2% |
| Platelets Transfusion Dependence | 19.5% | 10.3% |
| Median BM Blasts (min-max) | 7% (0-19%) | 5% (0-17%) |

Decitabine and cedazuridine were given as individual capsules of decitabine (35 mg) and CED (100 mg) in the dose escalation and dose expansion stages of Phase 1 and during the initial dose confirmation stage of Phase 2 and then as a single fixed-dose combination (FDC) tablet (ASTX727) of both decitabine (35 mg) and cedazuridine (100 mg) combined in the second stage of Phase 2 and in Phase 3. The composition of the ASTX727 FDC tablet used in the Phase 3 clinical study is shown in Table 5.

TABLE 5

Composition of ASTX727 Tablet

| Component | Function | Standard | Composition (% w/w) | Quantity (mg/tab) |
|---|---|---|---|---|
| Cedazuridine | Active | In-house specification | 19.42 | 100.0 |
| Decitabine | Active | In-house specification | 6.80 | 35.0 |
| Lactose monohydrate | Diluent | NF | 62.62 | 322.5 |
| Hypromellose | Binder | USP | 1.94 | 10.0 |
| Croscarmellose sodium | Disintegrant | NF | 4.85 | 25.0 |
| Colloidal silicon dioxide | Glidant | NF | 0.97 | 5.0 |
| Magnesium stearate | Lubricant | NF | 0.49 | 2.5 |
| Total Core Tablet | | | 97.09 | 500.0 |
| Opadry II 85F15458 Red | Film Coat | Supplier | 2.91 | 15.0 |
| Total Coated Tablet | | | 100.00 | 515.0 |

The plasma decitabine 5-day $AUC_{0-t}$ for the individual capsules of decitabine (35 mg) and cedazuridine (100 mg) is shown in Table 6A, and the plasma decitabine 5-day $AUC_{0-t}$ for the single ASTX727 tablet is shown in Table 6B.

TABLE 6A

Phase 2 PK (Cedazuridine + Decitabine Capsules vs IV DEC)

| | N | IV Geo. LSM | Oral Geo. LSM | Ratio of Geo. LSM Oral/IV, % (80% CI) | Intrasubject (% CV) |
|---|---|---|---|---|---|
| Decitabine 5-day $AUC_{0-t}$ (h · ng/ml) | 40 | 802.81 | 750.82 | 93.52 (82.10, 106.5) | 47.0 |

IV = 20 mg/m² IV infusion (1 h) of decitabine.
Oral = 100 mg cedazuridine and 35 mg decitabine capsules
CI = Confidence Interval;
IV = Intravenous;
Geo. LSM = Geometric Least Squares Means;
CV = coefficient of variation

TABLE 6B

Phase 2 PK (ASTX727 vs IV DEC)

| | N | IV Geo. LSM | Oral ASTX727 FDC Geo. LSM | Ratio of Geo. LSM Oral/IV, % (80% CI) | Intra-subject (% CV) |
|---|---|---|---|---|---|
| Decitabine 5-day $AUC_{0-t}$ (h · ng/ml) | 24 | 745.26 | 727.29 | 97.59% (80.48, 118.3) | 53.8 |

Figure 4:
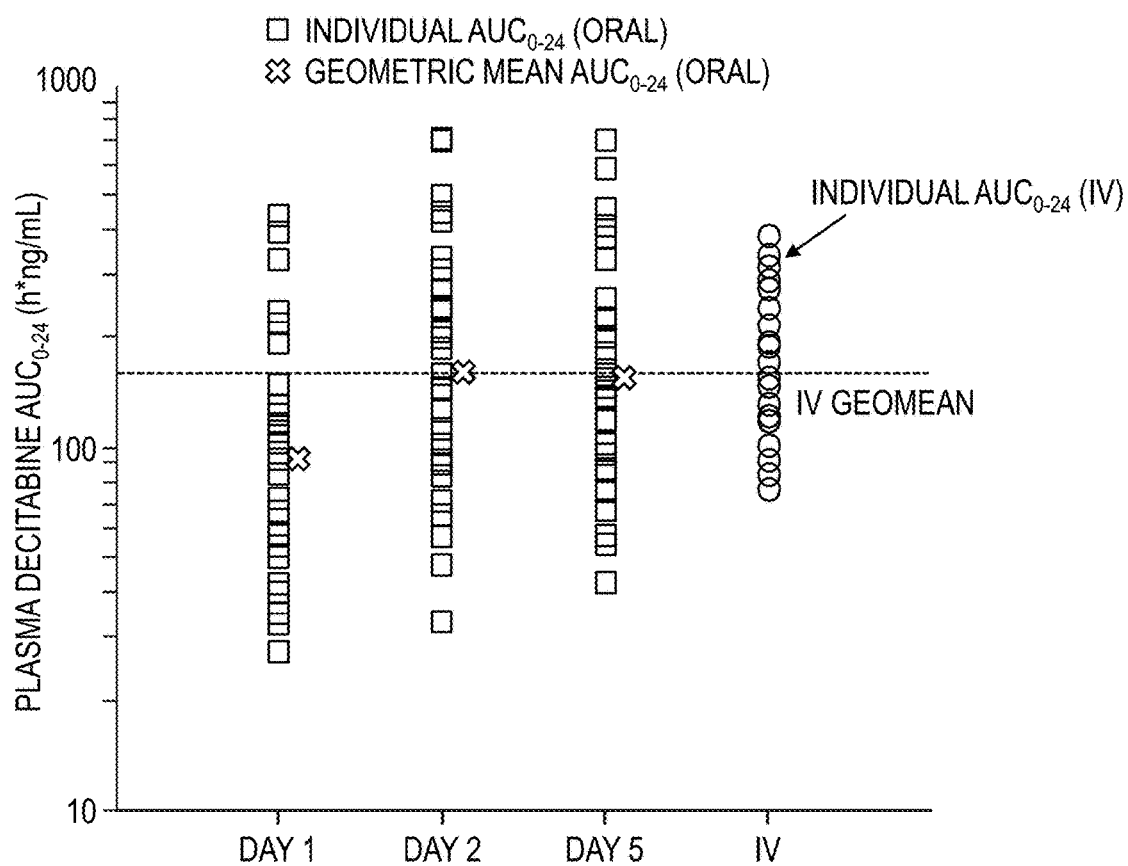
FIG. 4 shows the mean decitabine $AUC_{0\text{-}24}$ (h·ng/mL) at days 1, 2, and 5 for oral decitabine/cedazuridine and for IV decitabine in the Phase 2 study described in FIG. 3.
Figure 5A:
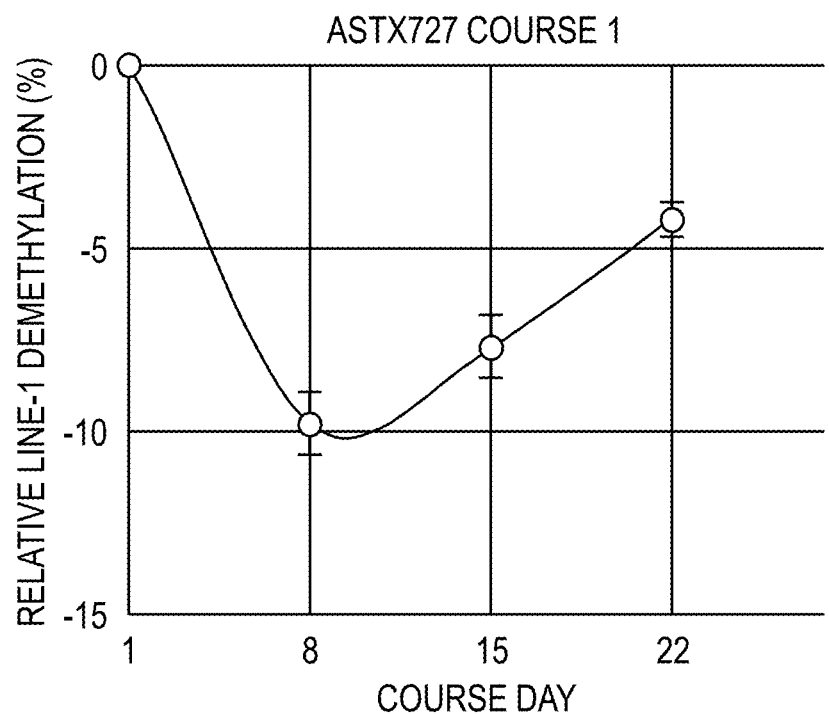
FIGS. 5A and 5B show the relative LINE-1 demethylation (%) for the sequence of ASTX727 (Cycle 1) to IV decitabine (Cycle 2) in the Phase 2 study described in FIG. 3.
Figure 5B:
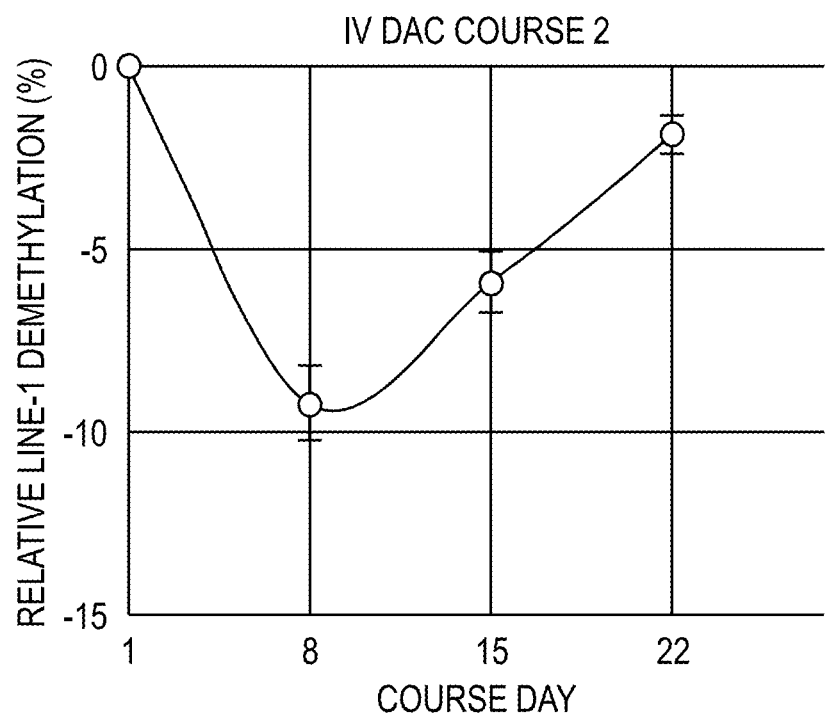
Figure 6A:
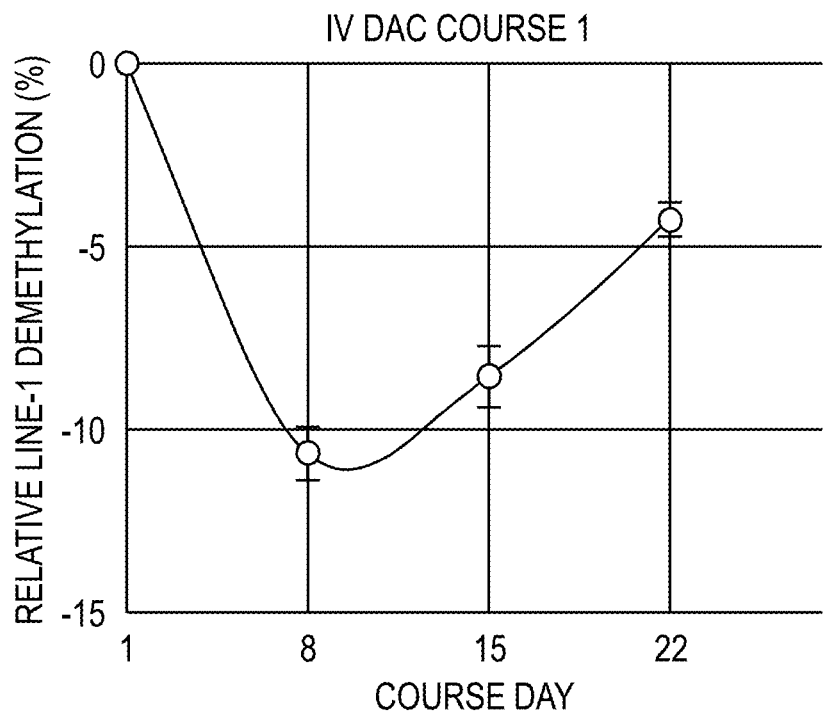
FIGS. 6A and 6B show the relative LINE-1 demethylation (%) for the sequence of IV decitabine (Cycle 1) to ASTX727 (Cycle 2) in the Phase 2 study described in FIG. 3.
Figure 6B:
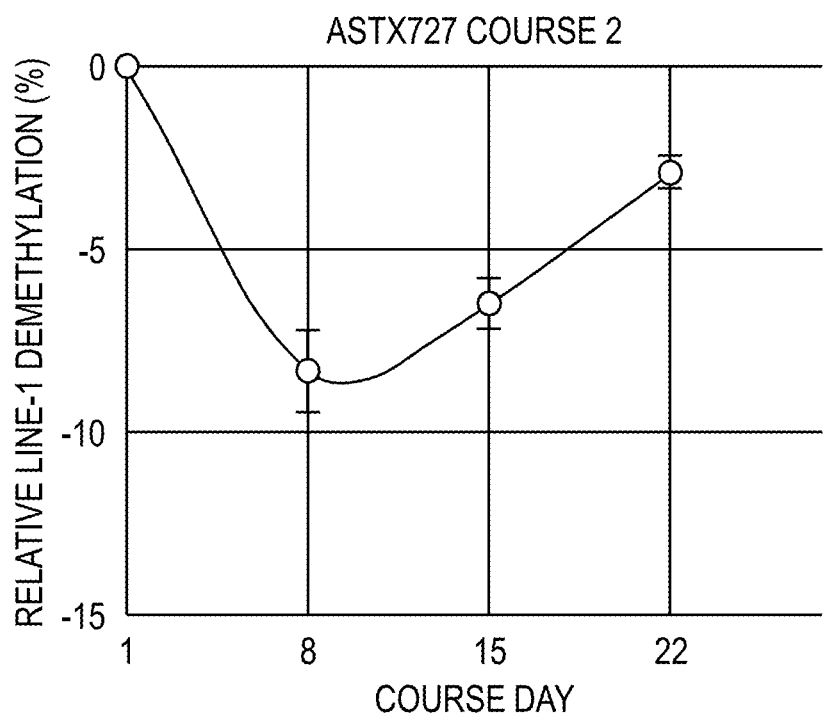

IV = 20 mg/m² IV infusion (1 h) of decitabine.
Oral = ASTX727 FDC tablet (100/35 mg cedazuridine/decitabine)
CI = Confidence Interval;
IV = Intravenous;
Geo. LSM = Geometric Least Squares Means;
CV = coefficient of variation FIG. 4 provides the individual and geometric mean plasma decitabine $AUC_{0-24}$ following oral 100 mg cedazuridine and 35 mg decitabine vs. a single infusion of decitabine 20 mg/m². The oral 5-day decitabine exposure was approximately 98% that of IV decitabine confirming that the doses selected for cedazuridine and decitabine in the tablet was a close match to IV decitabine.

Hematology and global DNA methylation were assessed on days 1, 8, 15, 22, and 29 of the first cycle with the long interspersed nuclear element-1 (LINE-1) methylation bisulphite sequencing assay (Yang, A S, Koshi K D, Choi S W, et al. DNA methylation changes after 5-aza-2-deoxycytidine therapy in patients with leukemia. Can. Res. 2006; 66; 5495-503). Changes in DNA methylation after treatment were expressed as relative change (%), calculated as: 100× ([methylation on a given post-treatment day]–[baseline methylation]. Adverse event assessments through physical examinations and laboratory monitoring (haematology, metabolic profile, and liver enzymes) were done before treatment on day 1 of each cycle (weekly for haematology in the first two cycles). While on treatment, patients were assessed for adverse events and clinical response, including haematology, metabolic profile, liver enzymes, directed physical examinations, vital signs, transfusion records, and dosing records. Once off treatment, patients were followed up for survival and transformation to acute myeloid leukemia. Dose reduction or delays were permitted at the investigators' discretion to allow for recovery from drug-related myelosuppression.

The results of the LINE-1 study are shown in FIGS. 5A-5B and 6A-6B. The Phase 2 Efficacy and Safety date for the study are shown in Tables 7 and 8, respectively.

TABLE 7

Phase 2 Efficacy (Best Response[a] and Transfusion Independence[b])

| Best Response (N = 80) | % | 95% CI |
|---|---|---|
| Complete Response (CR) | 21.3% | 13-32% |
| Partial Response | 0 | |
| Marrow Complete Response (mCR) | 22.5% | 14-32% |
| mCR + HI | 7.5% | 2.8-15.6% |
| Hematological Improvement (HI) | 16.3% | 9-26% |
| HI-E | 10% | 4-19% |
| HI-N | 2.5% | 0.3-8.7% |
| HI-P | 13.8% | 7-23% |
| Overall Response (CP + PR + mCR + HI) | 60% | 48-71% |
| RBC's Transfusion Independence (N = 38)[b] | 50% | 33-67% |
| Platelets Transfusion Independence (N = 12)[b] | 50% | 21-79% |

[a]IWG 2006 criteria;
[b]at least 8 weeks of transfusion independence in patients who were dependent at baseline

TABLE 8

Phase 2 Safety-Related AEs Grade ≥3 in ≥5% of Patients

| | IV DEC (Cycle 1 or 2) N = 75 n (%) | ASTX727 (Cycle 1 or 2) N = 78 n (%) |
|---|---|---|
| Any Grade ≥3 Related AEs | 24 (32%) | 21 (27%) |
| Neutropenia | 16 (21.3%) | 11 (14.1%) |
| Thrombocytopenia | 11 (14.7%) | 9 (11.5%) |
| Leukopenia | 6 (8.0%) | 6 (7.7%) |
| Anemia | 4 (5.3%) | 5 (6.4%) |
| Febrile Neutropenia | 4 (5.3%) | 3 (3.8%) |

Example 3: Phase 3 Study

Figure 7:
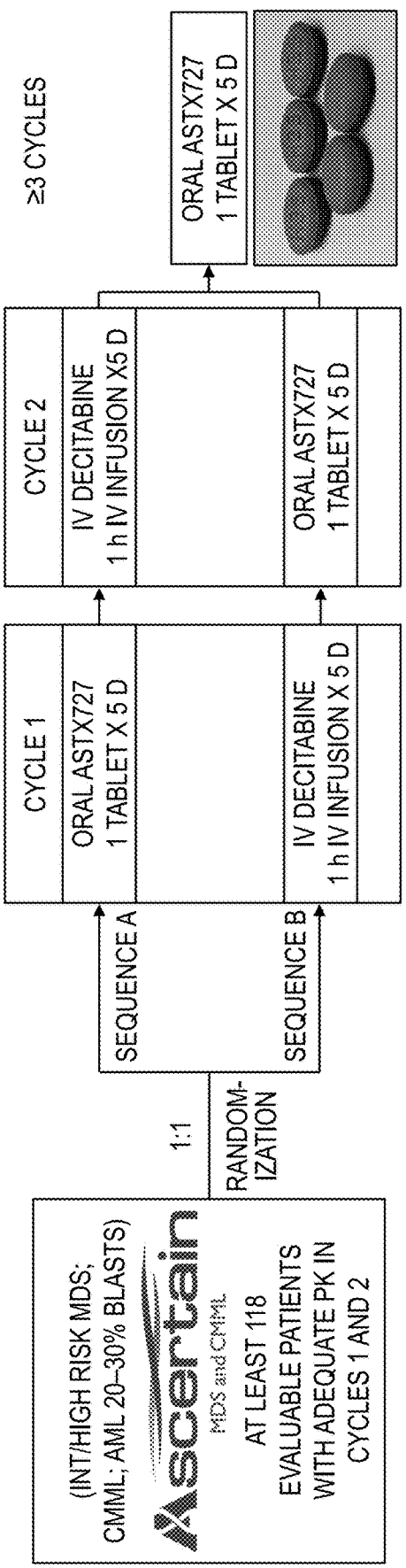
FIG. 7 is a graphic describing a Phase 3 randomized cross over study designed to establish equivalence to IV decitabine, efficacy, safety, and maximum LINE-1 demethylation for the ASTX727 oral dosage form.

Phase 3 was a randomized cross over design where MDS and CMML patients eligible to receive decitabine were randomized to Sequence A where they received ASTX727 in Cycle 1 then IV decitabine in Cycle 2, or Sequence B with the reverse order. All patients received ASTX727 from Cycle 3 onwards to assess long term efficacy and safety. 118 evaluable patients were needed to show AUC equivalence between oral and IV administrations. See FIG. 7. The major entry criteria for subjects: 1) candidates for IV decitabine; 2) ECOG PS 0-2; 3) Life expectancy of at least 3 months; 4) adequate organ function; and 5) one prior cycle of HMA is allowed. The primary endpoint included total plasma level 5-day decitabine AUC equivalence (Oral/IV 90% CI between 80% and 125%). The secondary endpoints were efficacy, including response rate, transfusion independence, duration of response, leukemia-free and overall survival; safety of ASTX727; and Max LINE-1 demethylation.

Of the 133 patients treated in Phase 3, 123 completed both IV and oral 5-day cycles to assess the decitabine AUC for both. The ratio of plasma 5-day decitabine AUC of oral/IV was approximately 99% with a 90% Confidence Interval of about 93% to 106%. Sensitivity and secondary analyses of all patients treated with PK assessments all confirmed the primary analysis results (See Table 9).

TABLE 9

Primary Endpoint (5-day Decitabine AUC Equivalence)

| | IV DEC | | Oral ASTX727 | | Ratio of Geo. | Intra- |
|---|---|---|---|---|---|---|
| 5-day $AUC_{0-24}$ (h · ng/ml) | N | Geo. LSM | N | Geo. LSM | LSM Oral/IV, % (90% CI) | subject (% CV) |
| Primary Paired[1] Analysis | 123 | 864.9 | 123 | 855.7 | 98.9 (92.7, 105.6) | 31.7 |

[1]Paired patient population: patients who received both ASTX727 and IV decitabine in the randomized first 2 cycles with adequate PK samples.

The study met its primary endpoint with high confidence: oral/IV plasma 5-day decitabine AUC ~99% with 90% CI of ~93-106%. All sensitivity and secondary PK AUC analyses confirmed findings from primary analysis.

Figure 8:
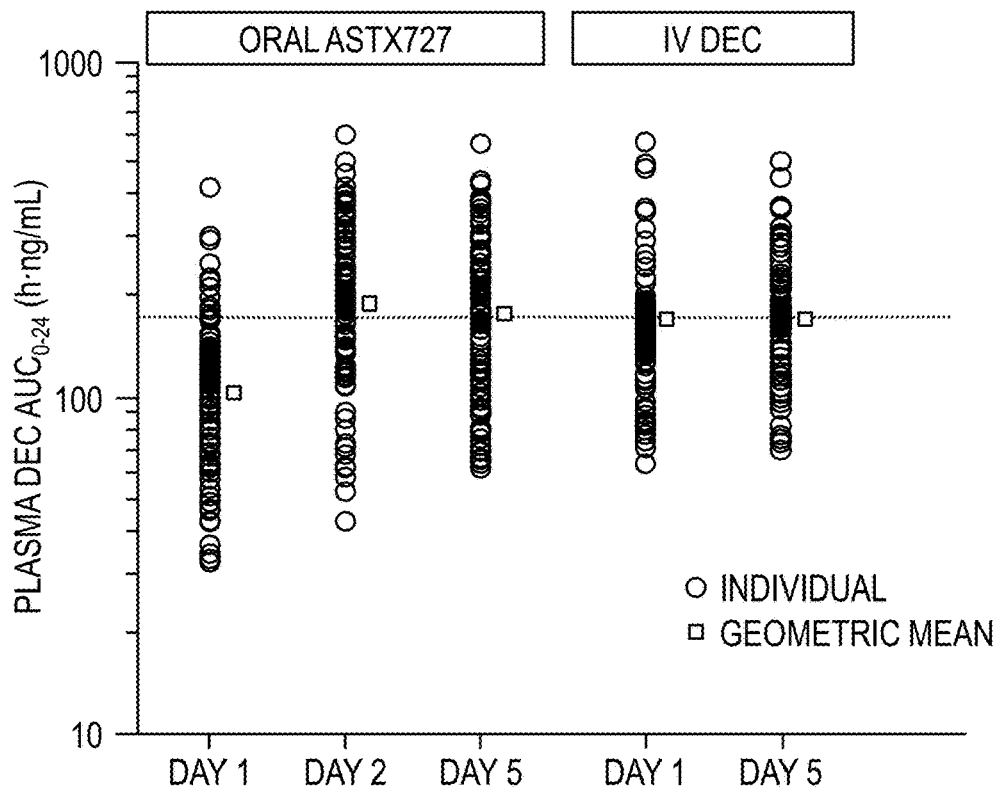
FIG. 8 shows the PK analysis for oral ASTX727 and IV decitabine in the Phase 3 study described in FIG. 7.

FIG. 8 shows the individual patient exposures for both ASTX727 at days 1, 2, and 5 and IV decitabine at days 1 and 5. As can be seen, the individual exposures of patients treated with either oral decitabine or IV decitabine largely overlap with each other despite oral decitabine being given at a fixed dose while IV is being given based on body surface area. The AUC for decitabine on day 1 is slightly lower than the AUC on days 2-5 and the AUC for IV administration. The ratio of AUC for decitabine on day 2 versus day 1 is about 1.5:1 to about 2:1.

Figure 9:
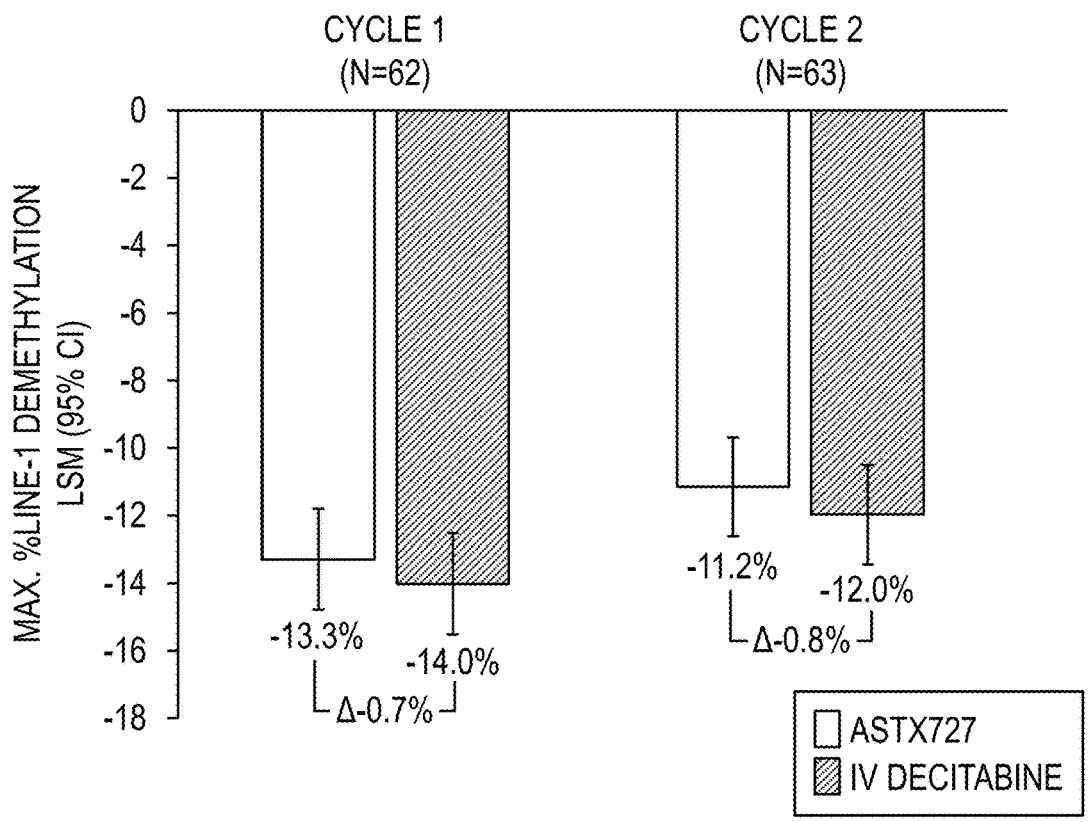
FIG. 9 provides the maximum LINE-1 demethylation LSM (95% CI) for both oral ASTX727 and IV decitabine during Cycle 1 and Cycle 2, as described in FIG. 7.

FIG. 9 shows the pharmacodynamic effect of global DNA demethylation as measured by LINE-1 assay was also almost identical when oral is compared to IV in cycles 1 and 2. The difference in DNA methylation between oral and IV was <1% and not significant.

In summary, the oral ASTX727 fixed-dose tablet (cedazuridine/decitabine 100/35 mg) achieved ~99% of plasma decitabine 5-day AUC systemic exposures compared with IV decitabine 20 mg/m$^2$ (primary endpoint). Furthermore, the robust results were confirmed in all AUC sensitivity and secondary analyses. Furthermore, the oral ASTX727 achieved almost identical pharmacodynamic effect to IV decitabine (<1% difference in LINE-1% DNA demethylation). Additionally, the durable clinical responses, 50% transfusion independence, and median survival of 18.3 months observed in Phase 2 with long term follow up are consistent with IV decitabine. Furthermore, no significant differences in adverse events including GI adverse events between oral ASTX727 and IV decitabine in the randomized first 2 cycles.

The foregoing is illustrative of the present invention, and is not to be construed as limiting thereof. The invention is defined by the following claims, with equivalents of the claims to be included therein.

What is claimed is:

1. A solid oral dosage form consisting of 100 mg cedazuridine, 35 mg decitabine, lactose monohydrate, hydroxypropyl methyl cellulose, croscarmellose sodium, colloidal silicon dioxide, and magnesium stearate, and optionally a coating, wherein the solid oral dosage form upon daily administration to a human provides plasma levels of decitabine with a 5-day AUC for decitabine that is equivalent to the 5-day AUC for a daily intravenous dose of decitabine of 20 mg/m$^2$ administered as a 1 h infusion.

2. The solid oral dosage form of claim 1, wherein upon daily administration to a human the ratio of AUC for decitabine on day 2 versus day 1 is about 1.5:1 to about 2:1.

3. The solid oral dosage form of claim 1, wherein the solid oral dosage form upon daily administration to a human provides a pharmacodynamic effect that is equivalent to the pharmacodynamic effect for a daily intravenous dose of decitabine of 20 mg/m$^2$ administered as a 1 h infusion.

4. The solid oral dosage form of claim 3, wherein the pharmacodynamic effect is DNA demethylation.

5. The solid oral dosage form of claim 1, which is a tablet.

6. The solid oral dosage form of claim 1, which is a capsule.

7. The solid oral dosage form of claim 1, wherein the solid oral dosage form comprises the coating.

8. The solid oral dosage form of claim 7, wherein the coating is a color coating.

9. The solid oral dosage form of claim 8, wherein the coating is Opadry II 85F15458 Red.

* * * * *